(12) United States Patent
Manhes

(10) Patent No.: US 6,402,715 B2
(45) Date of Patent: *Jun. 11, 2002

(54) SURGICAL INSTRUMENT SYSTEM

(75) Inventor: Hubert Manhes, Vichy (FR)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,743

(22) PCT Filed: Apr. 25, 1997

(86) PCT No.: PCT/DE97/00839

§ 371 (c)(1),
(2), (4) Date: Aug. 9, 1999

(87) PCT Pub. No.: WO97/40750

PCT Pub. Date: Nov. 6, 1997

(30) Foreign Application Priority Data

Apr. 25, 1996 (DE) .......................... 196 16 610

(51) Int. Cl.⁷ .................................................. A61M 1/00
(52) U.S. Cl. ..................... 604/35; 604/151; 600/156
(58) Field of Search .............................. 604/19, 22–23, 604/26–27, 35, 43, 48, 131, 151, 164.01, 902, 272, 500; 600/103, 156, 164, 171

(56) References Cited

U.S. PATENT DOCUMENTS 4,468,216 A * 8/1984 Muto ........................... 604/43
4,607,619 A * 8/1986 Seike et al.
4,825,865 A * 5/1989 Zelman
5,022,382 A * 6/1991 Ohshoji et al.
5,098,387 A * 3/1992 Wiest et al. ................ 604/153
5,392,765 A * 2/1995 Muller
5,449,357 A * 9/1995 Zinnanti
5,460,490 A * 10/1995 Carr et al.
5,540,677 A * 7/1996 Sinofsky ........................ 606/8

FOREIGN PATENT DOCUMENTS

| EP | 0537573 | * | 10/1991 |
| EP | 0 537 573 A2 | | 4/1993 |
| FR | 2 639 819 | | 6/1990 |
| GB | 2 161 725 A | | 1/1986 |
| WO | WO 94/11052 | | 5/1994 |
| WO | WO 95/10982 | * | 4/1995 |

* cited by examiner

Primary Examiner—Richard K. Seidel
Assistant Examiner—LoAn H. Thanh
(74) Attorney, Agent, or Firm—St. Onge Steward Johnston & Reens LLC

(57) ABSTRACT

A surgical instrument system, in particular, for use in non-endoscopic surgery having a surgical instrument provided with a shaft in which a supply channel having a distally disposed liquid emergence opening and an evacuation channel having a distally disposed liquid draw-off opening, and a pump device which pumps a liquid into the supply channel with such a pressure that the tissue in front of the distal end of the surgical instrument is separated along natural separation planes by the liquid emerging from the emergence opening, and the liquid out of the liquid bubble surrounding the distal end of the surgical instrument is pumped through the evacuation channel to the proximal end of the surgical instrument.

12 Claims, 2 Drawing Sheets

SURGICAL INSTRUMENT SYSTEM

DESCRIPTION

1. Technical Field

The present invention relates to a surgical instrument system, in particular, for use in non-endoscopic surgery.

2. State of the Art

In endoscopic surgery, the instruments are inserted into natural corporal cavities through existing or artificially created entrances. Thus, the corporal cavity can be "inflated" by means of a gas, for instance $CO_2$, during the surgical measure and in this manner create or maintain the "operation area" for the surgical procedure.

Conventional non-endoscopic surgery, i.e. surgery in which the human body is opened and the operation measures are not carried out in a natural corporal cavity, often anatomically given points of cutting are used to gain "access" into the body. Preferably, work is conducted along so-called planes of separation or cutting planes. Contrary to corporal cavities, the different possible planes of separation are interconnected so that it is, in particular, impossible to use a gas that is under pressure for expanding and for scavenging the area immediately surrounding the instrument. One problem in surgery is, i.a., to move the (surgical) instrument gently forward along such types of natural cutting planes respectively planes of separation in the body.

In the present description, cutting planes or planes of separation refer to, for example, areas where different corporal layers or tissue layers, such as for instance different muscle tissue (layers) or muscle tissue and fat tissue or fat tissue and veins are adjacent to each other. In plain words, these types of planes are the interfaces between different regions, of which each can, in particular, be homogeneous.

SUMMARY OF THE INVENTION

The object of the present invention is to create a surgical instrument system that can be used in the human body or in animal bodies, in particular, in conventional, non-endoscopic surgery and that can be moved forward in a simple manner along natural cutting planes or planes of separation.

An invented solution to this object is based on the knowledge that water, in circumstances containing dissolved substances, such as salts, etc., is an ideal distention element for widening or separating corporal tissue along interfaces respectively planes of separation.

An element of the present invention is therefore that after opening the body, i.e. after creating an entrance, a surgical instrument is inserted from whose distal end a liquid jet emerges which "widens" or "separates" the tissue so that a liquid bubble or a "water bubble" can move forward in the center of natural cutting planes, which allow the surgical instrument to advance, in particular, without severing homogeneous tissue regions.

The added liquid is pumped off again using such evacuation power that (preferably) only one liquid bubble forms surrounding the distal end of the surgical instrument. In this way, the instrument can be moved forward along a natural cutting plane or a plane of separation, and the separation plane is opened by the pressure of the emerging liquid to at least such a degree that the surgical instrument can be inserted and moved forward. On the other hand, the pumping off of the liquid through the liquid bubble prevents too much liquid from being introduced, which would "flood" the surgical field.

Therefore, the invented surgical instrument system, which is designed, in particular, for use in non-endoscopic surgery, is provided with a surgical instrument having a shaft in which a supply channel with a distally disposed emergence opening for the liquid and a evacuation channel with a distally disposed draw-off opening for the liquid are provided, and a pump device which pumps a liquid into the supply channel with such a pressure that the tissue in front of the distal end of the surgical instrument is separated along the natural planes of separation by the liquid emerging from the emergence opening, and which pumps the liquid out of the liquid bubble surrounding the distal end of the surgical instrument through the evacuation channel to the proximal end of the surgical instrument.

Preferably a surgical channel which permits the insertion of treatment instruments, such as instruments for cutting, expanding or coagulating, is provided in the shaft, in particular, in its center. In this way, the instrument not only can move forward along the planes of separation but surgery can also be performed without changing instruments.

In order to be able to observe the forward movement of the instrument as well as the performance of the surgical procedure, it is moreover preferred if the shaft is provided at with an endoscope optic or if the shaft is provided with a channel into which an endoscope optic can be inserted. In order to be able to observe the instrument advancing, in particular, if the endoscope optic is disposed off center, it is advantageous if the lens of the endoscope optic has a viewing direction optical axis respectively a lens-side optical axis which forms a small angle, which can be e.g., approximately 12°, with the longitudinal axis of the shaft.

Fundamentally, a variety of instruments, such as are in particular known from endoscopy, can be utilized as "surgical shaft instruments".

However, it is preferred if the shaft has the basic construction of a laparoscope with a laterally offset observation means or eyepiece so that there is one continuous channel in the laparoscope. According to the present invention, a twin hollow needle, in which the supply channel and the evacuation channel are provided, is inserted into this channel. Moreover, the surgical channel can also be provided in the twin hollow needle, preferably in the center. The central disposal of the surgical channel yields an advantageous rinsing of the instrument inserted into the surgical channel.

If using a twin hollow needle in which the supply channel and the evacuation channel are provided, it is furthermore preferred if these are provided with the two connections for the pump device. These connections can be constructed in a variety of ways, for example as Luer-lock connections.

The pump device, for example, can be a (Sero) conditioning pump, regulated by an electronic control unit. The control unit regulates, or controls the pressure under which the liquid emerges in such a manner that it is adapted to the consistency or the density of the tissue layers to be separated. In a number of applications, it is preferred if the pressure under which the liquid emerges is between approximately 0.1 bar and approximately 1 bar.

BRIEF DESCRIPTION OF THE DRAWING

The present invention is described in the following, without the intention of limiting the scope or spirit of the overall inventive idea, using preferred embodiments with reference to the drawing by way of example, to which reference is explicitly made with regard to all the invented details not disclosed herein. Depicted are in.

DESCRIPTION OF A PREFERRED EMBODIMENT

Figure 1:
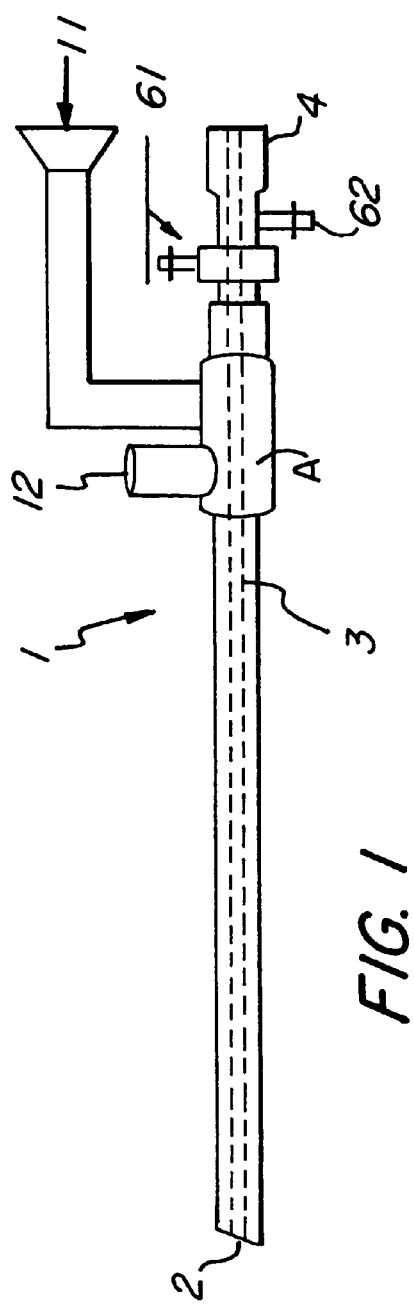
FIG. 1 a lateral view of an instrument employed according to the present invention, and FIG. 2 a twin hollow needle constructed according to the present invention.

FIG. 1 shows an instrument, which can be employed in accordance with the present invention as a "surgical shaft instrument".

This instrument has the basic construction of a known laparoscope 1 having a lateral viewing means or eyepiece 11 and a connection 12 for a light conductor cable by means of which the instrument is connected to a not depicted light source. The light from the light source illuminates the object field lying before the distal end 2 of the laparoscope 1, which can be viewed by means of lens, image conveyors, containing rod lens relay systems or image fiber bundles, none of which is shown for clarity and eyepiece 11. A video unit can be flanged, in a known manner, to an eyepiece 11.

Laparoscopes of this type are manufactured, for example, by Karl Storz GmbH & CO., Tuttlingen, Germany. For the explanation of all details not described in more detail herein, reference is explicitly made to the construction of these instruments.

In the illustrated preferred embodiment, the instrument is provided with an endoscope lens having an oblique lens-side optical axis. The lens side forms preferably an angle of approximately 12° with the instrument axis A.

Moreover, laparoscope 1 is provided, in an as such known manner, with a centrally disposed channel 3 which connects the distal end 2 with the proximal end 4 of instrument 1 and into which other instruments can be inserted.

An element of the present invention is that a special hollow needle 31, which is depicted in more detail in FIG. 2 and is described in more detail below, can be inserted into channel 3.

Figure 2:
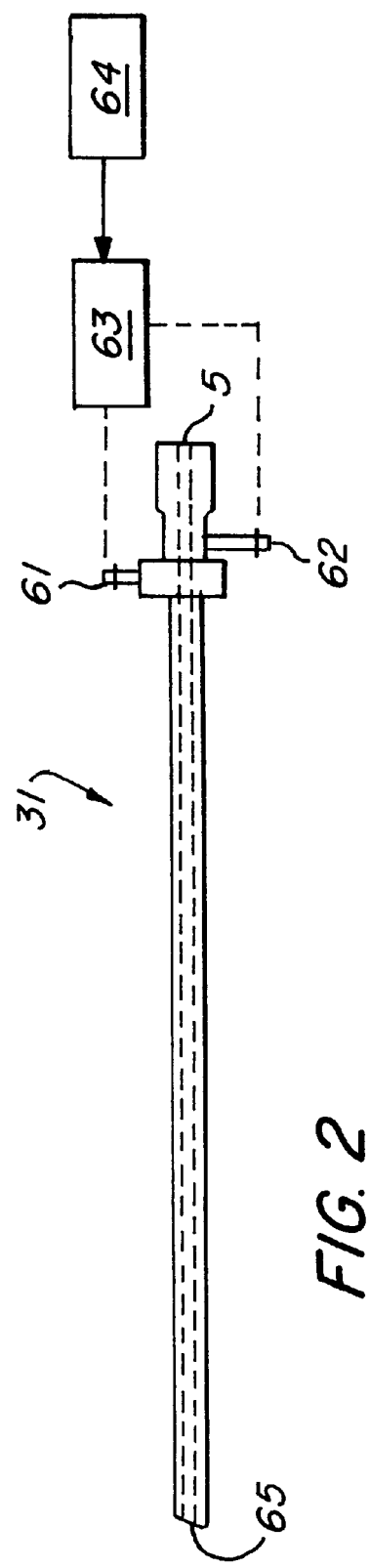

Hollow needle 31 depicted in more detail in FIG. 2 is inserted into laparoscope 1 and preferably connected to it via an as such known standard coupling. Hollow needle 31 is provided with a channel 5 through which the different instruments, such as dissecting instruments, scissors, HF instruments etc., required for performing a surgical procedure can be conveyed to distal end 2.

Figure 3:
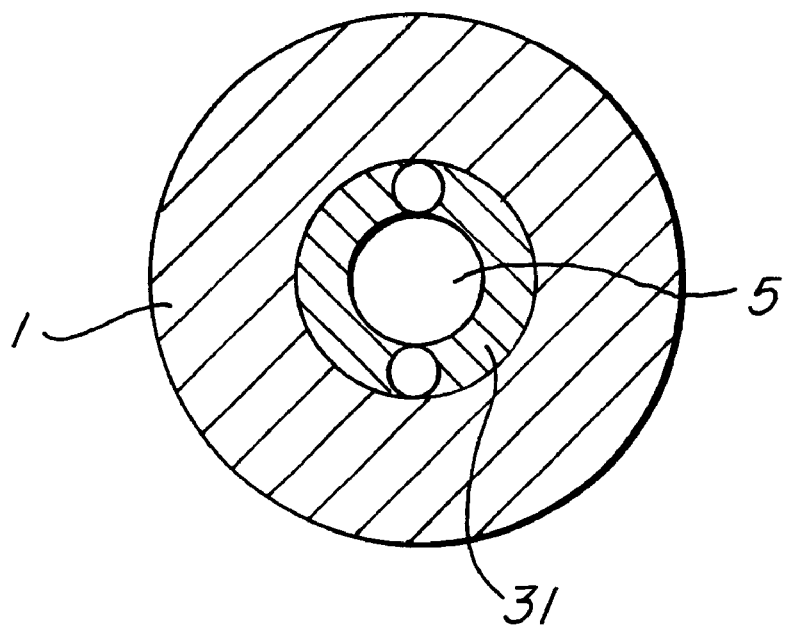
FIG. 3 is a cross sectional view of the twin hollow needle of FIG. 2.

Furthermore, hollow needle 31 can be provided with two hollow channels, which are diagrammatically depicted in FIG. 3 and of which one is a supply channel 10 for a liquid with a distally disposed liquid emergence opening and the other 12 is a evacuation channel with a distally disposed liquid draw-off opening. Further, the needle 31 can have a central channel 14 provided for receiving an surgical instrument.

These two channels can, in particular, be disposed on opposite sides of channel 5.

The supply channel 10 and the evacuation channel 12 are connected via two Luer connections 61 and 62 with a pump device 63, which can preferably be a pump of the type Sero conditioning pump.

Furthermore, an electronic control unit 64 is provided which regulates the pump device. The control unit, in particular, regulates the pressure with which the fluid, which, in particular, can be water in circumstances containing additives, emerges from the distally disposed emergence opening 65, and with which the liquid from the liquid bubble surrounding the distal end 2 of the instrument is drawn off. In dependence on the density and the consistency of the to-be-separated tissue, the pressure with which the liquid emerges can typically range between 0.1 bar and 1 bar. These pressures are distinctly higher than the pressures employed in the fields of endoscopy and, in particular, laparoscopy for continuous rinsing, as are for example described in U.S. Pat. No. 5,392,765.

An element of the present invention is that the pump unit 63, used to rinse and evacuate, creates a water bubble which expands the tissue along natural separation planes. This "water bubble" permits moving the instrument combination (laparoscope, hollow needle and instrument)forward into the tissue.

Thanks to the 12° oblique optic, the surgeon continuously sees the employed instrument, which in particular can be somewhat longer than the channel into which the instrument is inserted.

In the preceding, the present invention is described using a preferred embodiment. Of course, a variety of different modifications are possible within the scope of general inventive idea:

Thus, the distal emergence opening of the supply channel can be constructed as a nozzle in order to increase the efficiency of the "water-jet cutting" respectively "water-jet separation" performed according to the present invention.

Furthermore, the given pressure values are not restricting; in individual cases exceeding them or falling short is possible.

What is claimed is:

1. A surgical instrument system comprising:
   an elongate shaft with a proximal end and a distal end for insertion into a human or animal body to be treated, the shaft being provided therein with a supply channel for a liquid, the supply channel having a distally disposed liquid emergence opening, and an evacuation channel having a distally disposed liquid draw-off opening;
   a pump device connected to a proximal end of the supply channel for pumping a liquid into the supply channel so that the liquid emerges from the emergence opening at the distal end, and also connected to the proximal end of the evacuation channel for drawing-off liquid surrounding the distal end of the evacuation channel through the evacuation channel; and
   an electronic control unit which controls the pump device so that the pressure with which the liquid emerges from the emergence opening and the pressure with which the liquid is drawn into the evacuation channel are such as to maintain a bubble of liquid at the end of the instrument.

2. A surgical instrument system according to claim 1 characterized by the fact that said shaft further includes a viewing channel, said viewing channel receiving an endoscope optic.

3. A surgical instrument system according to claim 2, characterized by the fact that the lens of said endoscope optic has one viewing direction which forms a small angle with the longitudinal axis of said shaft.

4. A surgical instrument system according to claim 4, characterized by the fact that said small angle is approximately 12°.

5. A surgical instrument system according to claim 1, characterized by the fact that said shaft further includes a surgical channel passing therethrough which is adapted to receive a treatment instrument.

6. A surgical instrument system according to claim 5, characterized by the fact that said surgical channel is provided in the center of said shaft.

7. A surgical instrument system according to claim 1 characterized by the fact that said shaft has the basic construction of a laparoscope having a laterally offset viewing.

8. A surgical instrument system according to claim 1, characterized by the fact that said liquid is water.

9. A surgical instrument system according to claim 1, characterized by the fact that said pressure under which said liquid emerges ranges between approximately 0.1 and approximately 1 bar.

10. A surgical instrument system according to claim 1, characterized by the fact that the pressure with which said liquid emerges from the emergence opening is adapted to the consistency or density of the to-be-separated tissue layers.

11. A surgical process for separating tissue comprising the steps of:

opening a body to expose the tissue;

inserting an instrument provided with supply and evacuation channels, said channels having a liquid emergence opening and a draw-off opening, respectively, which are distally disposed;

forming a bubble of the liquid by controllably pumping liquid through the supply channel and out the emergence opening through the evacuation channel simultaneously; and moving the instrument to separate the tissue along the natural separation planes.

12. The surgical process of claim 11 including the step of pumping liquid out of the body through the draw-off opening.

* * * * *